(12) United States Patent
Benner et al.

(10) Patent No.: US 9,062,345 B1
(45) Date of Patent: Jun. 23, 2015

(54) PROCESSES FOR SYNTHESIZING DNA WITH NON-STANDARD NUCLEOTIDES

(71) Applicant: Steven A Benner, Gainesville, FL (US)

(72) Inventors: Steven A Benner, Gainesville, FL (US); Daniel Hutter, Gainesville, FL (US)

( * ) Notice: Subject to any disclaimer, the term of this patent is extended or adjusted under 35 U.S.C. 154(b) by 0 days.

(21) Appl. No.: 14/138,532

(22) Filed: Jan. 15, 2014

Related U.S. Application Data

(63) Continuation-in-part of application No. 12/999,138, filed as application No. PCT/US2009/003595 on Jun. 16, 2009, now Pat. No. 8,614,072.

(60) Provisional application No. 61/132,225, filed on Jun. 17, 2008.

(51) Int. Cl.
*C12Q 1/68* (2006.01)
*C12P 19/34* (2006.01)

(52) U.S. Cl.
CPC .............. *C12Q 1/6853* (2013.01); *C12P 19/34* (2013.01); *C12Q 2525/117* (2013.01); *C12Q 2521/101* (2013.01)

(58) Field of Classification Search
CPC ........... C12Q 1/6853; C12Q 2525/117; C12Q 2521/101
USPC ......................................... 435/6.1, 91.1, 91.2
See application file for complete search history.

*Primary Examiner* — Jezia Riley

(57) ABSTRACT

The disclosed invention provides processes to synthesize DNA analogs that contain non-standard nucleotides, defined as those which form nucleobase pairs that fit standard Watson-Crick geometry, but are joined to their complements by hydrogen bonding patterns different from those that join standard A:T and G:C pairs. The disclosed process resembles "rolling circle amplification", but uses primers that contain non-standard nucleotides, as well as 2'-deoxynucleotide triphosphates whose heterocyclic "nucleobases" are also non-standard. An example is provided that shows this process using 6-amino-5-nitro-3-(1'-beta-D-2'-deoxyribofuranosyl)-2(1H)-pyridone to implement the non-standard "small" donor-donor-acceptor (pyDDA) hydrogen bonding pattern, and 2-amino-8-(1'-beta-D-2'-deoxyribofuranosyl)-imidazo[1,2-a]-1,3,5-triazin-4(8H)-one to implement the "large" acceptor-acceptor-donor (puAAD) pattern.

14 Claims, 5 Drawing Sheets pyADD                          puDAA pyDAD                          puADA pyDDA                          puAAD

SEQUENCE LISTING

```
<160> NUMBER OF SEQ ID NOS: 3

<210> SEQ ID NO 1
<211> LENGTH: 99
<212> TYPE: DNA
<213> ORGANISM: Artificial Sequence
<220> FEATURE:
<221> NAME/KEY: misc_feature
<222> LOCATION: (12)..(12)
<223> OTHER INFORMATION: n = p, nonstandard nucleotide of the invention
<220> FEATURE:
<221> NAME/KEY: misc_feature
<222> LOCATION: (15)..(15)
<223> OTHER INFORMATION: n = p, nonstandard nucleotide of the invention
<220> FEATURE:
<221> NAME/KEY: misc_feature
<222> LOCATION: (18)..(18)
<223> OTHER INFORMATION: n = p, nonstandard nucleotide of the invention
<220> FEATURE:
<221> NAME/KEY: misc_feature
<222> LOCATION: (80)..(80)
<223> OTHER INFORMATION: n = p, nonstandard nucleotide of the invention
<220> FEATURE:
<221> NAME/KEY: misc_feature
<222> LOCATION: (83)..(83)
<223> OTHER INFORMATION: n = p, nonstandard nucleotide of the invention
<220> FEATURE:
<221> NAME/KEY: misc_feature
<222> LOCATION: (86)..(86)
<223> OTHER INFORMATION: n = p, nonstandard nucleotide of the invention
<220> FEATURE:
<223> OTHER INFORMATION: Synthetic

<400> SEQUENCE: 1
tggcgtaggc angantgncc atcatcaggc tctcacacag cataacattc cttagttcgc    60
tataggactt tcactcaagn ttntgntagt tggagctga                           99

<210> SEQ ID NO 2
<211> LENGTH: 10
<212> TYPE: DNA
<213> ORGANISM: Artificial Sequence
<220> FEATURE:
<221> NAME/KEY: misc_feature
<222> LOCATION: (1)..(1)
<223> OTHER INFORMATION: n = z, nonstandard nucleotide of the invention
<220> FEATURE:
<221> NAME/KEY: misc_feature
<222> LOCATION: (4)..(4)
<223> OTHER INFORMATION: n = z, nonstandard nucleotide of the invention
<220> FEATURE:
<221> NAME/KEY: misc_feature
<222> LOCATION: (7)..(7)
<223> OTHER INFORMATION: n = z, nonstandard nucleotide of the invention
```

```
<220> FEATURE:
<223> OTHER INFORMATION: Synthetic

<400> SEQUENCE: 2 ncantcntgc                                                          10

<210> SEQ ID NO 3
<211> LENGTH: 10
<212> TYPE: DNA
<213> ORGANISM: Artificial Sequence
<220> FEATURE:
<221> NAME/KEY: misc_feature
<222> LOCATION: (1)..(1)
<223> OTHER INFORMATION: n = p, nonstandard nucleotide of the invention
<220> FEATURE:
<221> NAME/KEY: misc_feature
<222> LOCATION: (4)..(4)
<223> OTHER INFORMATION: n = p, nonstandard nucleotide of the invention
<220> FEATURE:
<221> NAME/KEY: misc_feature
<222> LOCATION: (7)..(7)
<223> OTHER INFORMATION: n = p, nonstandard nucleotide of the invention
<220> FEATURE:
<223> OTHER INFORMATION: Synthetic

<400> SEQUENCE: 3 nttntgntag                                                          10
```

US 9,062,345 B1

PROCESSES FOR SYNTHESIZING DNA WITH NON-STANDARD NUCLEOTIDES

CROSS REFERENCE TO RELATED APPLICATIONS

This application claims benefit of U.S. patent application Ser. No. 12/999,138, which was the U.S. national stage application of International Patent Application No. PCT/US2009/003595, filed Jun. 16, 2009, which claims the benefit of U.S. Provisional Patent Application No. 61/132,225, filed Jun. 17, 2008, the disclosures of which are hereby incorporated by reference in their entirety, including all figures, tables and sequences.

STATEMENT REGARDING FEDERALLY SPONSORED RESEARCH OR DEVELOPMENT

This invention was made with government support under a grant awarded by the United States Defense Advanced Research Project Agency (R0011-11-2-0018) and the National Institute of Allergy and Infectious Diseases (R01AI098616). The government has certain rights in the invention.

THE NAMES OF THE PARTIES TO A JOINT RESEARCH AGREEMENT

Not applicable.

INCORPORATION-BY-REFERENCE OF MATERIAL SUBMITTED ON A COMPACT DISC

None

BACKGROUND OF THE INVENTION

1. Field of the Invention

This invention relates to rolling circle amplification processes that incorporate nucleotide analogs ("non-standard nucleotides") that form base pairs joined by hydrogen bonding patterns not found in standard nucleotides A, T, G and C.

2. Description of Related Art

Natural oligonucleotides bind to complementary oligonucleotides according to well-known rules of nucleobase pairing first elaborated by Watson and Crick, where adenine (A) pairs with thymine (T) (or uracil, U, in RNA), and guanine (G) pairs with cytosine (C), with anti-parallel complementary strands. In this disclosure, "DNA", "oligonucleotide", or "nucleic acid" is understood to include DNA and RNA, as well as derivatives where the sugar is modified, as in 2'-O-methyl and 2',3'-dideoxynucleoside derivatives, where the nucleobase has an appendage, and these nucleic acids and their analogs in non-linear topologies, including as dendrimers, comb-structures, and nanostructures, and analogs carrying appendages or tags (e.g., fluorescent, functionalized, or binding, such as biotin). Further, "polymerase" in this application is meant to include DNA polymerases of all families, RNA polymerases, and reverse transcriptases.

These pairing rules allow specific hybridization of oligonucleotides to complementary oligonucleotides, making oligonucleotides valuable as probes in the laboratory, in diagnostics, as messages that direct the synthesis of proteins, and in other applications known in the art. Such pairing is used, for example and without limitation, to capture oligonucleotides to beads, arrays, and other solid supports, allow nucleic acids to fold in hairpins, beacons, and catalysts, support function, such as fluorescence, quenching, binding/capture, and catalysis, and as part of complex structures, including dendrimers and nanostructures, and scaffolds to guide chemical reactions.

Further, base pairing underlies the enzymatic synthesis of oligonucleotides complementary to a template. Here, assembly of building blocks from nucleoside triphosphates is directed by a template to form a complementary oligonucleotide with a complementary sequence. This is the basis for replication in living systems, and underlies technologies for enzymatic synthesis and amplification of specific nucleic acids by enzymes such as DNA and RNA polymerase, the polymerase chain reaction (PCR), and assays involving synthesis, ligation, cleavage, immobilization and release, inter alia.

Watson-Crick pairing rules can be understood as the product of two rules of complementarity: (1) size complementarity (a big purine pairs with a small pyrimidine) and (2) hydrogen bonding complementarity (hydrogen bond donors pair with hydrogen bond acceptors). However, as noted by U.S. Pat. Nos. 5,432,272, 5,965,364, 6,001,983, 6,037,120, 6,140,496, 6,627,456, and 6,617,106, Watson-Crick geometry can accommodate as many as 12 nucleobases forming 6 mutually exclusive pairs. Of these, four nucleobases forming two pairs are designated "standard", while eight nucleobases forming four pairs were termed "non-standard", and may be part of an "artificially expanded genetic information system" (AEGIS).

To systematize the nomenclature for the hydrogen bonding patterns, the hydrogen bonding pattern implemented on a small component of a nucleobase pair are designated by the prefix "py". Following this prefix is the order, from the major to the minor groove, of hydrogen bond acceptor (A) and donor (D) groups. Thus, both thymine and uracil implement the standard hydrogen bonding pattern pyADA. The standard nucleobase cytosine implements the standard hydrogen bonding pattern pyDAA. Hydrogen bonding patterns implemented on the large component of the nucleobase pair are designated by the prefix "pu". Following the prefix, hydrogen bond donor and acceptor groups are designated, from major to minor groove, by "A" and "D". Thus, the standard nucleobases adenine and guanine implement the standard hydrogen bonding patterns puDA- and puADD respectively.

A central teaching of this disclosure is that hydrogen-bonding patterns are distinct from the organic molecule that implements them. Thus, guanosine implements the puADD hydrogen-bonding pattern. So does, however, 7-deazaguanosine, 3,7-dideazaguanosine, and many other purines and purine analogs, including those that carry side chains carrying functional groups, such as biotin, fluorescent, and quencher groups. Which organic molecule is chosen to implement a specific hydrogen-bonding pattern determines, in part, the utility of the non-standard hydrogen-bonding pattern, in various applications to which it might be applied.

As described by U.S. Ser. No. 12/999,138, which is incorporated in its entirety by reference, claims of U.S. Pat. No. 5,432,272 and its successors covered non-standard bases that implemented the pyDDA hydrogen bonding pattern that encountered problems, including epimerization, oxidation, and uncharacterized decomposition. Accordingly, Benner invented a new non-standard nucleoside, 6-amino-5-nitro-3-(1'-beta-D-T-deoxyribofuranosyl)-2(1H)-pyridone (trivially designated as dZ when incorporated into sequences) to implement the pyDDA hydrogen bonding pattern. The nitro group rendered the otherwise electron-rich heterocycle stable against both oxidation and epimerization under standard conditions. When paired with a corresponding puAAD nucleotide, duplexes were formed with stabilities that, in many cases, were higher than those observed in comparable strands incorporating the dG:dC nucleobase pair. This invention is covered by U.S. Pat. No. 8,053,212, which is incorporated herein in its entirety by reference.

While Z supports binding of oligonucleotide analogs containing it to complementary strands that match a nucleobase implementing the puAAD hydrogen bond pattern, it was not clear that polymerases would accept this unnatural base pair. Polymerases are known to be idiosyncratic, meaning that experimentation is necessary to ascertain whether a specific implementation of a non-standard hydrogen bonding scheme can be accepted by a polymerase. This includes special architectures by which dZ:dP pairs might be synthesized in duplex oligonucleotides using various polymerases. These include PCR and nested PCR, termed "higher level PCR" architectures in U.S. patent application Ser. No. 12/999,138. These require thermal cycling to separate duplexes in each cycle of amplification.

Another architectures is known in the art as "rolling circle amplification" (RCA) [Dean, F. B., Nelson, J. R., Giesler, T. L., Lasken, R. S. (2001) Rapid amplification of plasmid and phage DNA using Phi29 DNA polymerase and multiply-primed rolling circle amplification. *Genome Research* 11, 1095-1099] [Johne, R., Mueller, H., Rector, A., can Ranst, M., Steven, H. (2009) Rolling-circle amplification of viral DNA genomes. *Trends Microbiol.* 17, 205-211.] using phi29 polymerase. These references are hereby incorporated herein in their entireties by reference.

In contrast to various PCR architectures, RCA does not require thermal cycling. Therefore, RCA does not require a thermostable polymerase. Rather, RCA uses a cyclic single stranded DNA molecule as a template. A primer is annealed to this cyclic single stranded DNA. Then, a polymerase that does strand displacement extends the primer to give a long single stranded product that is a concatamer of the segments that complement the circular template.

It is known in the art that dZ nucleotide incorporated into an oligonucleotide supports binding of oligonucleotides containing it to a complementary strand that incorporates at a matched position a nucleobase implementing the puAAD hydrogen bond pattern, it was not clear that polymerases would accept this unnatural base pair. Polymerases are known to be idiosyncratic [Horlacher, J., Hottiger, M., Podust, V. N., Huebscher, U., Benner, S. A. (1995) Expanding the genetic alphabet: Recognition by viral and cellular DNA polymerases of nucleosides bearing bases with non-standard hydrogen bonding patterns. *Proc. Natl. Acad. Sci.*, 92, 6329-6333], meaning that experimentation is necessary to ascertain whether a specific implementation of a non-standard hydrogen bonding scheme can be accepted by a polymerase that is not a close homolog of a polymerase that has already been experimentally examined. In the applications for which priority is claimed, this is shown for thermostable polymerases of Family A and Family B. This disclosure reports data showing that the pair between dZ and dP is also formed in duplex DNA by strand-displacing polymerases used in a rolling circle polymerase synthesis.

BRIEF SUMMARY OF THE INVENTION

This invention concerns processes that create oligonucleotides by rolling circle amplification, or RCA, where the products contain one or more non-standard nucleotides in the product DNA molecule(s) (FIG. 1).

DETAILED DESCRIPTION OF THE INVENTION

Figure 1A:
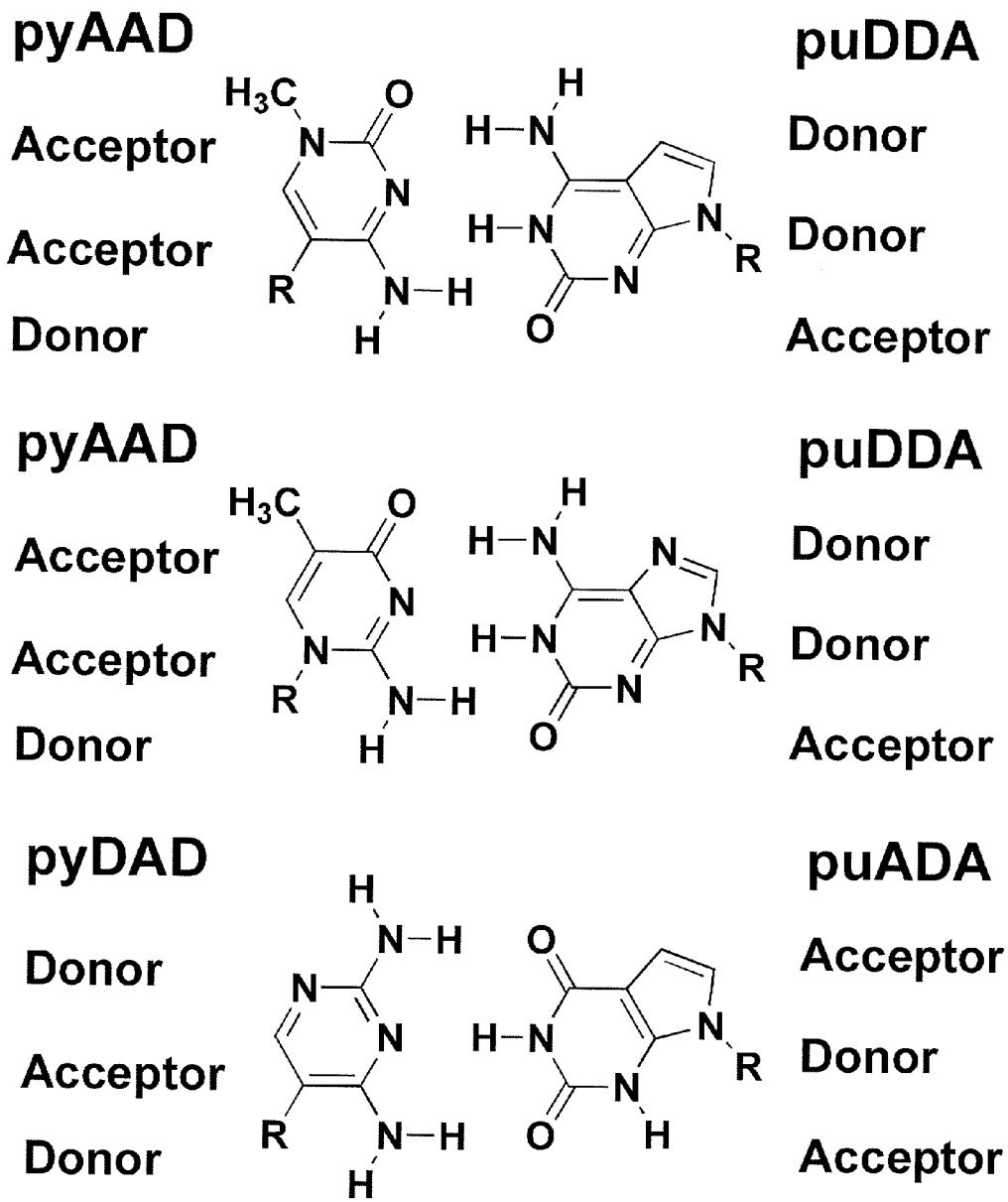
FIG. 1. A set of heterocycles implementing non-standard hydrogen bonding patterns, defined as those different from the hydrogen bonding patterns presented to a complementary strand by natural guanine, cytosine, thymine (or uracil), or adenine (or 2-aminoadenine). In the shorthand nomenclature, heterocycles that have a single six-membered ring are designated by "py" (as in "pyrimidine") followed by A or D to designate hydrogen bond acceptor or donor units. Since all of the aforementioned heterocycles could not easily fit on one page, they are divided into two drawings, labeled FIG. 1A and FIG. 1B.
Figure 1B:
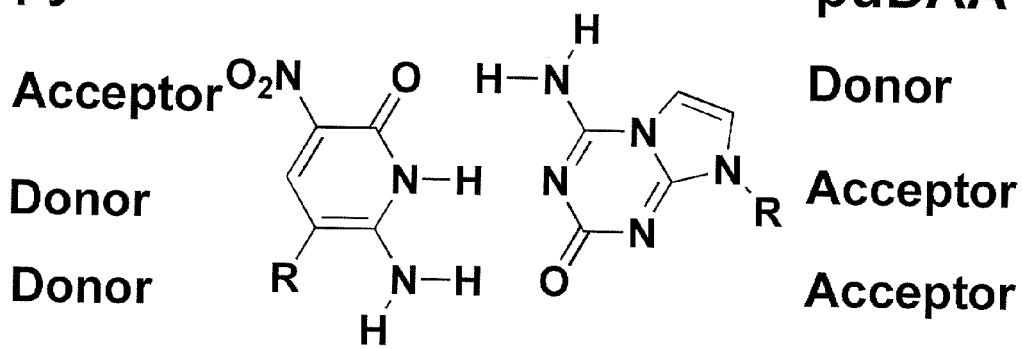
Figure 1B:
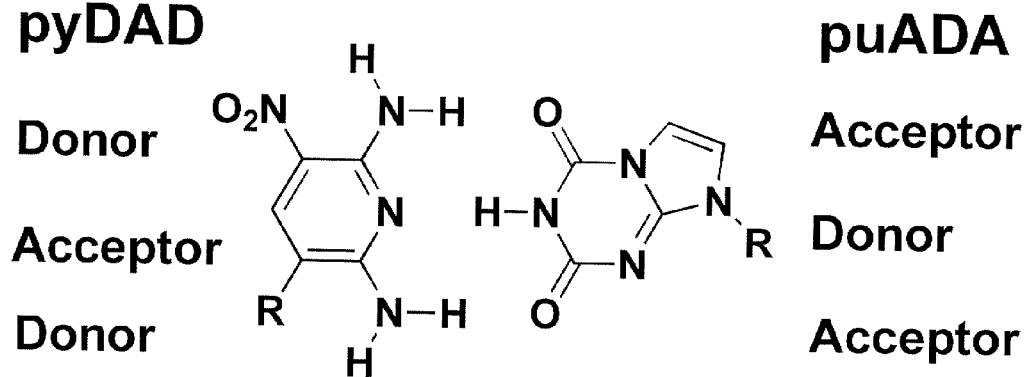
Figure 1B:
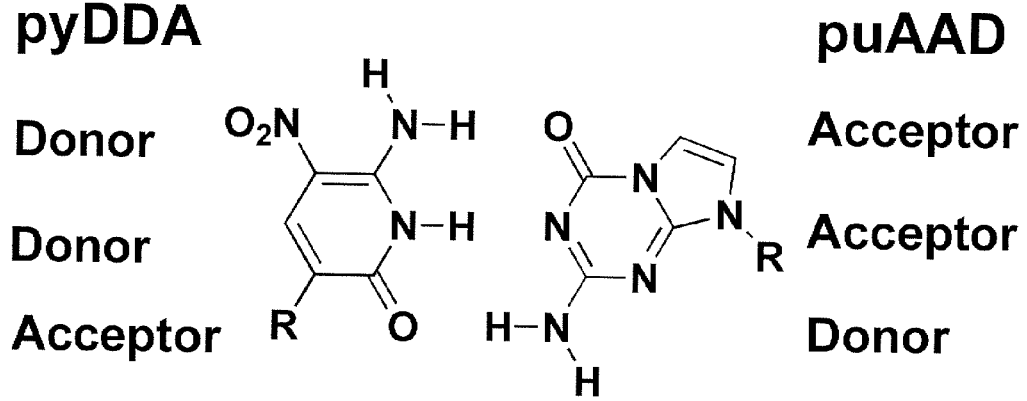
Figure 2:
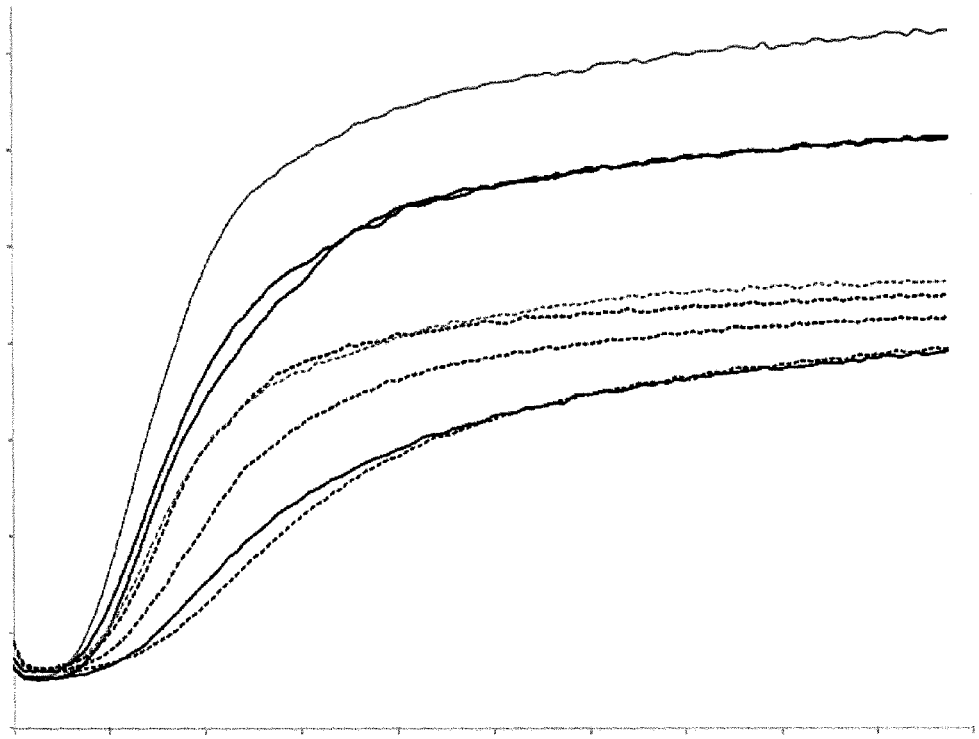
FIG. 2. Synthesis of DNA containing dZ using a "rolling circle amplification (RCA) process, with circularized SEQ ID NO 1 as the template. Shown is fluorescence (vertical axis) as a function of time (horizontal axis, tics are at two hour intervals), in both the "linear" format (dotted lines, SEQ ID NO 2 as the primer) and "exponential" format (solid lines, with both SEQ ID NO 2 and SEQ ID NO 3 as primers). This demonstrates the enablement of the claimed process. Different curves show the reduction in the rate of signal formation and the amount of final signal with increasing concentrations of dZTP (0.1, 0.3, 0.5, and 1.0 mM, from top to bottom). The results from this experiment were used to determine the presently preferred amount of dZTP to be used in the production of DNA using a rolling circle process.
Figure 3:
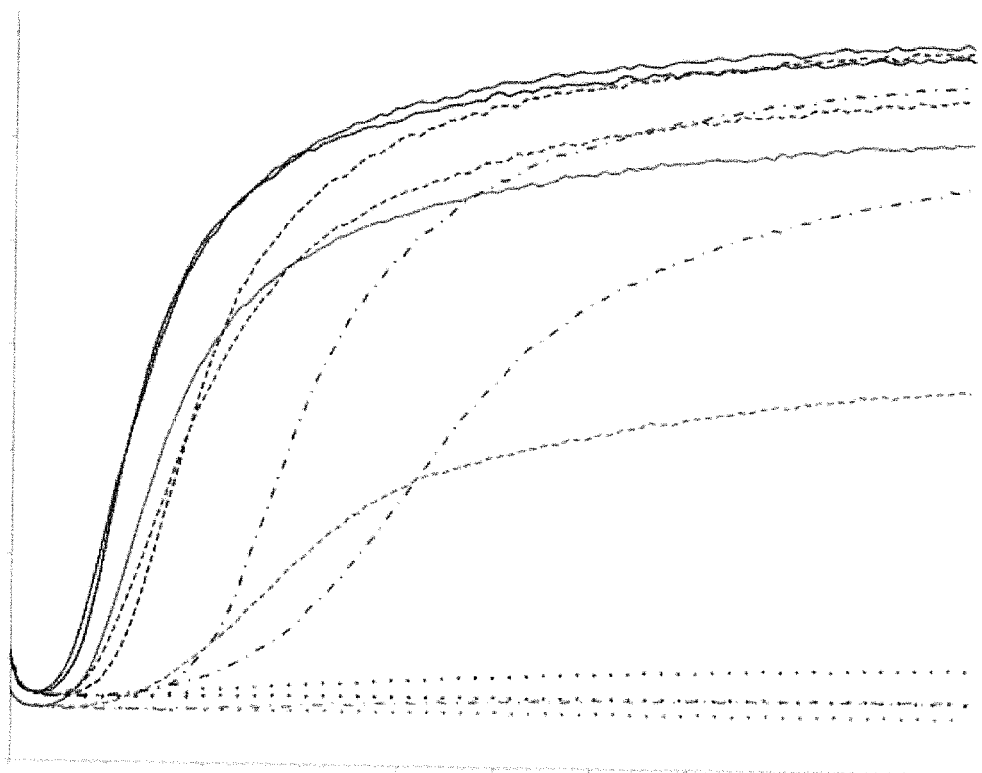
FIG. 3. Experiments determining the level of detection (LOD) of the RCA process targeting circles in decreasing amounts: 1 picomolar (solid lines), 100 femtomolar (----), 10 femtomolar (-·-·), and 1 femtomolar ( . . . ). The top three solid curves exploit (in the order from the top to bottom) an entirely natural circularized template, a circularized template containing one unnatural phosphate replacement (not at issue here), and the circularized template containing multiple dPs derived from SEQ ID NO 1. This shows that the signal is modestly lower with the template containing multiple dPs. This was also observed with lower levels of template.

Practicing this invention involves the following prescriptive steps, which parallel closely the process well known in the art as "rolling circle amplification (RCA):

1. Obtain a circularized DNA molecule that will serve as a template for the synthesis of the product oligonucleotide. This can be obtained either from natural sources, or by the circularization of a linear molecule that is obtained by synthesis. How this circularized DNA is obtained is not an object of the instant invention. The circular DNA is generally presented to the RCA process as a single stranded species. However, if a strand displacing polymerase is used, part or all of the circular DNA can be double stranded.

2. Anneal a primer to the circular DNA. This is typically termed in the art to be a "forward primer".

3. Treat the complex comprising the annealed primer and the circular template with a DNA polymerase and the requisite triphosphates. What triphosphates are "requisite" is determined by the nucleotides in the circular template. In standard RCA, these nucleotides are generally the standard 2'-deoxyguanosine, adenosine, cytidine, and thymidine. However, as is the case in the instant invention, the template contains one or more non-standard nucleotides (FIG. 1). In this case, the requisite triphosphates include those that complement the nonstandard nucleotides in the circular template.

4. Incubate the complex. If the polymerase used does not displace strands, the product will be a complementary oligonucleotide that renders the circular DNA a duplex, with a single nick (in the absence of a 5'-phosphate on the primer and ligase activity). If, however, the polymerase chosen is "strand-displacing", primer extension will continue, yielding a product that is a linear concatamer of the complementary oligonucleotide. As many copies will be concatenated, this process is often referred to as "amplification".

5. Optionally, introduce a second primer into the process. This second primer, often called the "reverse" primer, is complementary to the complementary oligonucleotide product. Therefore, it anneals to the concatenated oligonucleotides and initiates copying in the reverse direction. When the primer being extended on one concatemeric unit encounters a reverse primer annealed downstream, the downstream product is also displaced.

6. Detect the formation of the products. This can be done in multiple ways, as is well understood in the art. Here, the method of obtaining a signal does not require inventive steps.

The process of the instant invention differs in that the circularized template contains one or more non-standard nucleotides, defined as those that bind to their complements in a double helix using non-standard hydrogen bonding patterns, patterns different from those that hold together the G:C and A:T nucleobase pairs. The presently preferred non-standard pair is between 6-amino-5-nitro(1H)-pyridone (implementing the puAAD hydrogen bonding pattern in the dZ nucleoside) and 2-aminoimidazo[1,2-a]-1,3,5-triazin-4(8H)-one (implementing the puAAD hydrogen bonding pattern in the dP nucleoside). Also preferred is the pair between the nucleobases isoguanine and/or 7-deazaisoguanine, both implementing the puDDA hydrogen bonding patterns in their respective nucleosides, and the pyAAD nucleosides isocytidine and/or pseudocytidine in their 2'-deoxy forms.

The presently preferred polymerase is the Phi29 DNA polymerase. This polymerase is strand-displacing. It also has an exonuclease activity. Accordingly, the presently preferred primers contain thiophosphate linkages joining the 3'-nucleosides, instead of the standard phosphate linkages. The presently preferred number of these is two.

In the instant invention, the primer (or primers) can bind to the circular template either in segments that contain non-standard nucleotides, or outside of those segments. If the primer (or primers) bind to the circular template in a segment (or segments) that contain non-standard nucleotides, then the primers themselves must contain the complementary non-standard nucleotides, and the triphosphate pool must contain the requisite non-standard nucleoside triphosphates.

EXAMPLE 1

Rolling Circle Amplification with dZ and dP

Molecular Species:
6-Amino-5-nitro-3-(1'-beta-D-2'-deoxyribofuranosyl)-2 (1H)-pyridone ((implementing pyDDA, as dZ) and 2-amino-8-(1'-β-D-2'-deoxyribofuranosyl)-imidazo[1,2-a]-1,3,5-triazin-4(8H)-one (implementing puAAD, as dP) were obtained as both their 5'-triphosphates and their protected phosphoramidite derivatives suitable for chemical oligonucleotides synthesis, by procedures well known in the art.

A single stranded DNA molecule was prepared in cyclic form containing multiple dP's by cyclizing the following molecule, su, using standard phosphoramidite-based solid phase DNA synthesis, as well as other procedures well known in the art.

```
                                                SEQ ID 1
5'-TGG CGT AGG CAP GAP TGP CCA TCA TCA GGC TCT CAC

ACA GCA TAA CAT TCC TTA GTT CGC TAT AGG ACT TTC

ACT CAA GPT TPT GPT AGT TGG AGC TGA-3'

SEQ ID NO 2
5'-ZCAZTCZTGC-3'

SEQ ID NO 3
5'-PTTPTGPTAG-3'
```

The primer in SEQ ID NO 2 is complementary to the sequence G CAP GAP TGP in SEQ ID NO 1, which is underlined. One or more of its 3'-phosphate linkers are synthesized as thiophosphonate, known in the art to stabilize the primer against digestion by exonucleases, to manage the known exonuclease activity of the Phi29 DNA polymerase. This primer was used in "linear" RCA, which generates the long linear concatamer of DNA complementary to the circular form of SEQ ID NO 1.

SEQ ID NO 3 is, of course, identical to PTTPTGPTAG sequence in the cyclic structure which is underlined. Therefore, it will prime on the product of the rolling circle primer extension, allowing for "exponential" RCA. One or more of its 3'-phosphate linkers are also synthesized as thiophosphosphate, also known in the art to stabilize the primer against digestion by exonucleases. The presently preferred primers have two thiophosphate linkages at their 3'-ends, to confer for exonuclease resistance.

Linear RCA Reactions:

RCA reactions were run on a BioTek Synergy HT instrument (Software Gen5 version 2.00.17) at 30° C. for 48 h. The progress of the RCA was monitored by measuring the emergence of fluorescence (485/528) every 10 min arising from the binding of SYBR green I (Invitrogen) to newly formed duplex DNA. Separate experiments showed that neither dZ nor dP inhibited fluorescence.

The incubations were run with a final volume of 50 µL in 384-well plate at 30° C. The incubation mixtures contained Phi29 DNA polymerase (0.4 U/µL, New England Biolabs), manufacturer's Phi29 buffer (1x, containing 50 mM Tris-HCl, 10 mM $MgCl_2$, 10 mM $(NH_4)_2SO_4$, 4 mM DTT, pH 7.5 when measured at 25° C. dye), SYBR green I (from Invitrogen, 10,000x in DMSO; diluted to a final formal concentration of 0.2x; the final RCA mixture therefore contains 0.3 mM DMSO), the natural nucleoside triphosphates (10 mM each, all from Promega), dZTP (Firebird Biomolecular Sciences, 10 mM in $H_2O$), and dPTP (10 mM) in $H_2O$. Various experiments examined included linear RCA with 100 pM circle and 1000 nM primer (SEQ ID NO 2 only), exponential RCA with 1 pM circle and 100 nM of each primer (SEQ ID NO 2 and SEQ ID NO 3). The impact of varying amounts of dZTP and dPTP was examined. These are the most expensive compounds in the mix, but are needed in smaller amounts (compared to the natural nucleoside triphosphates). These experiments showed that higher dZTP and dPTP concentrations gave lower signals. These results suggest that excess of these triphosphates inhibit the amplification process. Further experiments showed that excess dZTP, not excess dPTP, inhibited the process. Accordingly, the presently preferred concentrations of dZTP and dPTP are (for linear RCA) 0.1-0.5 mM. The presently preferred concentrations of natural nucleoside triphosphates is 2 mM.

Exponential RCA Reactions:

For exponential RCA, the output signal was found (as is known in the art) to depend on the ratio of the concentrations of forward (SEQ ID NO 2) to reverse primer (SEQ ID NO 3). This is understood in the art as a consequence of the complexity of the process of exponential RCA. Its linear component extends SEQ ID NO 2 continuously, generating a linearly increasing number of points where SEQ ID NO 3 can bind and "reverse prime". At each, the reverse primer can anneal, initiating the formation of a duplex, which, in turn, will be invaded by the forward primer to give branched products. This generates a "bell-shaped" dependence of the product formation on the primer concentrations and ratio; too much of either primer will prematurely end the process prematurely.

In this example, the ratio was shown by experiment to not be different when dZ and/or dP is present. The presently preferred amount of primers for exponential RCA was (for each) 400 nM.

Figure 4:
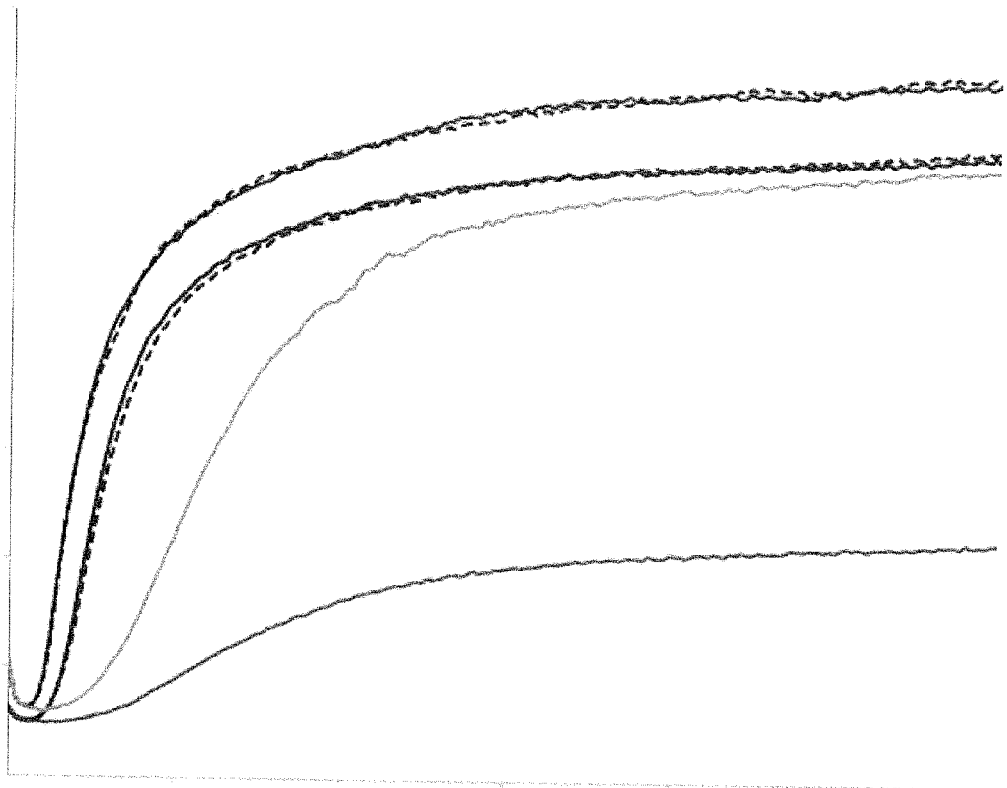
FIG. 4. Experiments showing the utility of using primers containing non-standard nucleotides in lowering the noise (false positive) in the appearance of a signal. Solid and dashed curves (overlapping) at the top show the amplification of an entirely natural circularized template with natural primers, and the circularized template obtained from SEQ ID NO 1. The next lower curve shows the "background noise" arising when natural primers are incubated under RCA conditions with a template that binds the primer nowhere explicitly. The bottom line shows the negligible amount of signal arising when primers containing dP are incubated under RCA conditions with a template that binds the primer nowhere explicitly.

Utility of RCA Reactions Containing Non-Standard Nucleotides:

Oligonucleotides containing non-standard nucleotides (such as those shown in FIG. 1) cannot find closely matched complements within natural DNA (found in all complex biological mixtures). The increasing fraction of non-standard components, the less possibility for "off target" annealing and priming. With classical RCA, "false positive" background is often seen, believed in the art to arise from off target priming. This utility is shown in FIG. 4.

What is claimed is:

1. A process for synthesizing an oligonucleotide sequence, said process comprising (a) contacting a primer with a circular DNA template in aqueous solution under conditions where said primer anneals to a complementary segment of said template, and (b) incubating said solution with a strand-displacing DNA polymerase and requisite 2'-deoxynucleoside triphosphates, wherein said template contains at least one non-standard nucleotide incorporating a heterocycle selected from the group consisting of the structures in FIG. 1a and FIG. 1b.

2. The process of claim 1, wherein said heterocycle is selected from the group consisting of

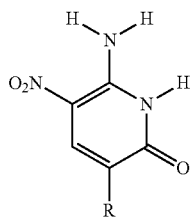

and

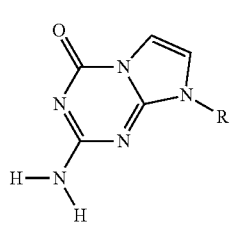

wherein R indicates the point of attachment of said heterocycle to the primer.

3. The process of claim 1 wherein said DNA polymerase is the Phi29 DNA polymerase.

4. The process of claim 2 wherein said DNA polymerase is the Phi29 DNA polymerase.

5. The process of claim 1 that also comprises incubation with a second reverse primer that anneals to a complementary segment of the product of said process.

6. The process of claim 5, wherein said heterocycle is selected from the group consisting of

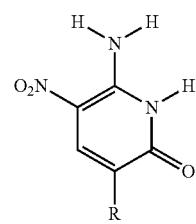

and

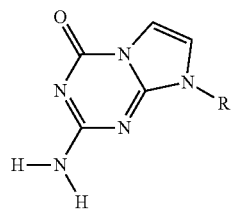

wherein R indicates the point of attachment of said heterocycle to the primer.

7. The process of claim 5 wherein said DNA polymerase is the Phi29 DNA polymerase.

8. The process of claim 6 wherein said DNA polymerase is the Phi29 DNA polymerase.

9. The process of claim 1 wherein said primer anneals to at least one non-standard nucleotide.

10. The process of claim 9 wherein the heterocycle of said non-standard nucleotide is selected from the group consisting of

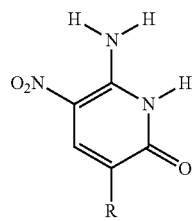

and

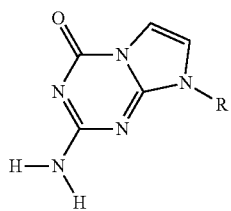

wherein R indicates the point of attachment of said heterocycle to the primer.

11. The process of claim 9 wherein said DNA polymerase is the Phi29 DNA polymerase.

12. The process of claim 10 wherein said DNA polymerase is the Phi29 DNA polymerase.

13. The process of claim 9 that also comprises incubation with a second reverse primer that anneals to a complementary segment of the product of said process.

14. The process of claim 12 that also comprises incubation with a second reverse primer that anneals to a complementary segment of the product of said process.

* * * * *